United States Patent
Kamijo

(10) Patent No.: US 7,136,055 B2
(45) Date of Patent: Nov. 14, 2006

(54) METHOD OF INDEXING SEIZURE RISK DUE TO FLASHING LIGHTS ON VIDEO DISPLAY AND SYSTEM THEREFOR

(75) Inventor: Kenichi Kamijo, Tokyo (JP)

(73) Assignee: NEC Corporation, Tokyo (JP)

( * ) Notice: Subject to any disclaimer, the term of this patent is extended or adjusted under 35 U.S.C. 154(b) by 323 days.

(21) Appl. No.: 10/453,549

(22) Filed: Jun. 4, 2003

(65) Prior Publication Data
US 2004/0155872 A1 Aug. 12, 2004

(30) Foreign Application Priority Data
Feb. 12, 2003 (JP) ............................. 2003-034309

(51) Int. Cl.
*G09G 5/60* (2006.01)
(52) U.S. Cl. .................... 345/204; 345/694; 345/214; 348/607; 348/571; 348/910
(58) Field of Classification Search ................ 345/204, 345/694, 214, 55, 72; 348/607, 571, 910
See application file for complete search history.

(56) References Cited

U.S. PATENT DOCUMENTS 3,993,976 A * 11/1976 Ginsburg ..................... 382/211

FOREIGN PATENT DOCUMENTS

| EP | 1 069 765 | 1/2001 |
|---|---|---|
| EP | 1 103 945 | 5/2001 |
| JP | A 80286653 | 11/1996 |
| JP | EP 1 103 945 A2 * | 5/2001 |
| JP | A 2001-154648 | 6/2001 |

* cited by examiner

*Primary Examiner*—Richard Hjerpe
*Assistant Examiner*—Leonid Shapiro
(74) *Attorney, Agent, or Firm*—Young & Thompson

(57) ABSTRACT

In order to generate a risk index of stress symptoms triggered by flashing lights on a scan type video display screen, a video signal processor is provided which operates such as to implement temporal filtering and spatial filtering on a video signal applied thereto every field and detect low temporal frequency components while excluding effects due to high spatial frequencies. A risk index generator receives the low frequency components from the video signal processor and determines the risk index based thereon.

25 Claims, 5 Drawing Sheets

FIG. 3

PIXEL VALUES RETRIEVED FROM FIELD MEMORY 42

| 12 | 20 | 20 | 10 | 10 | 20 |
|----|----|----|----|----|----|
| 20 | 10 | 50 | 40 | 30 | 10 |
| 10 | 20 | 40 | 10 | 40 | 10 |
| 20 | 40 | 20 | 10 | 20 | 10 |
| 10 | 10 | 30 | 40 | 20 | 10 |
| 10 | 30 | 20 | 50 | 30 | 20 |

PIXEL VALUE $*$

| 1 | 1 | 1 |
|---|---|---|
| 1 | 2 | 1 |
| 1 | 1 | 1 |

$\times \frac{1}{10} =$

LOW-PASS FILTER COEFFICIENT

OUTPUT OF ARITHMETIC CIRCUIT 46

| 7  | 13 | 17 | 17 | 13 | 9  |
|----|----|----|----|----|----|
| 11 | 20 | 29 | 29 | 21 | 13 |
| 14 | 25 | 27 | 26 | 21 | 13 |
| 14 | 25 | 23 | 22 | 18 | 12 |
| 15 | 21 | 27 | 27 | 22 | 12 |
| 8  | 15 | 20 | 24 | 20 | 10 |

PIXEL VALUE

METHOD OF INDEXING SEIZURE RISK DUE TO FLASHING LIGHTS ON VIDEO DISPLAY AND SYSTEM THEREFOR

BACKGROUND OF THE INVENTION

1. Field of the Invention

The present invention relates generally to technologies for indexing a risk of severe stress symptoms triggered by flashing, colorful lights displayed on video display terminal (VDT) such as a television, a computer terminal, etc.

2. Description of Related Art

With the recent developments of computer graphics techniques including virtual reality, a variety of images are displayed on a video screen of a television, computer terminal, etc., and the bright flashing lights of a a TV cartoon (for example) became a serious matter of triggering seizures or seizure-like symptoms. It is reported that flickers or flashes at a rate ranging from 2 to 55 Hertz is liable to induce seizures, various convulsions, vomiting, irritated eyes and other symptoms in certain photosensitive people. It is further reported that there is some evidence that flickering outside the 2–55 Hertz range can also cause seizures.

One approach to reducing or preventing such stress symptoms triggered by violent flickering or flashing is disclosed in the Laid-opened Japanese Patent Application No. 8-286653 (first prior art). According to this prior art, the video image signals whose brightness changes at about 10 Hertz are adaptively reduced using a temporal low-pass filterer and displaying the temporal frequency-treated images on the screen. However, this prior art suffers from the difficulties that the images displayed after being temporally filtered are deteriorated due to the reduction of frequency components of the moving pictures.

In order to overcome the above-mentioned problem, it has been proposed to generate a risk index signal in connection with the video signals which might cause the sever stress symptoms such as seizures. This proposal is disclosed in Japanese Patent Application P2001-154648A (second prior art) filed by the same entity as the assignee of the present application, in accordance with which upon detecting the video images which are likely to induce the sever stresses, an alarm or a warning signal is issued to alert viewers, Accordingly, it is possible to avoid the undesirable deterioration of the reproduced images.

Before turning to the present invention, it is deemed preferable to describe the second prior art with reference to FIG. 1.

FIG. 1 is a diagram schematically showing functional blocks for generating a VDT seizure risk index and relevant part of television receiver set.

In the following, the severe stress symptoms may be referred to as VDT seizures or simply seizures for the convenience of descriptions.

A primary-color signal generator 10 is supplied with a luminance signal Y and three color-difference signals R-Y, G-Y, and B-Y. The generator 10 produces three primary-color signals R, G, and B which are applied to a display unit (not shown). In addition, the primary-color signals R, G, and B are respectively applied to signal processing sections 12, 14, and 16. The outputs of the sections 12, 14, and 16 are fed to a VDT seizure risk index generator 18.

The signal processing sections 12, 14, and 16 are identical with one another in terms of the circuit configurations and the functions thereof, and as such, only the section 12 is illustrated in detail in FIG. 1. The section 12 generally comprises an analog-to-digital (A/D) converter 20, a field memory 22, and a temporal low-pass filter 24 which in turn comprises three field memories 26, 28, and 30, and an arithmetic circuit 32.

The field signals (analog) of primary-color R are applied to the analog-to-digital (A/D) converter 20 and converted to the corresponding digital field signals thereat without distinction between adjacent fields. The A/D converter 20 applies the digital field signals to the field memories 22 and 26 one by one.

In the interlaced scanning, one frame consists of two fields (odd and even fields), and the frame rate is about 30 per second and the field rate (or flash rate) is about 60 per second in the NTSC (the National Television System Committee) color transmission system. The arithmetic circuit 32 retrieves a field signal from the field memory 26 and also retrieves the previous field signal from the field memory 28, and calculates new pixel values based on the corresponding pixel values of the two-field signals obtained form the field memories 26 and 28 using the following equation (1)

$$Ii'(t)=(1-\delta)\times Ii(t)+\delta\times Ii(t-\Delta t) \qquad (1)$$

where i denotes a two-dimensional coordinate used to represent the position of each pixel in the field, Ii(t) denotes a pixel value in the coordinate i at a time t, $\Delta t$ denotes a time interval between two fields ($\Delta t=\frac{1}{60}$ seconds in the NTSC color transmission system), and $\delta$ is a coefficient ($0<\delta\leq 1$) which determines the characteristics of the temporal low-pass filter 24 and is typically set to 0.7 by way of example.

As shown in the above, the arithmetic circuit 32 operates such as to weight Ii(t) and Ii(t–$\Delta$t) by the coefficient (1–$\delta$) and $\delta$ respectively and then adds the multiplication results. The new pixel values thus calculated over one whole field are successively cumulated in the field memory 30. It is understood that the low temporal frequency components over the successive fields can be determined from the cumulated pixel values.

The VDT seizure risk index generator 18 is supplied with the pixel data from the field memories 22 and 30. In addition, the generator 18 receives the pixel data similar to those stored in the field memories 22 and 30 from the signal processing units 14 and 16, and calculates a,seizure risk index e(t) using the following equation (2)

$$e(t) = \frac{\sum_c \sum_i w_c |I_i(t) - I'_i(t)|^m}{N \times (I\ max)^m \times \sum_c w_c} \qquad (2)$$

where (1) $w_O$ represents weighting coefficients $w_R$, $w_G$, and $w_B$ ($0<w_R, w_G, w_B \leq 1$) of respective primary-color signals R, G, and B;

(2) Ii(t) denotes a pixel value at a time t in the coordinate i with respect to the primary color signals R, G and B;

(3) Ii'(t) is determined using equation (1);

(4) Imax denotes the maximal value of each pixel, and in case each pixel is represented by 8 bits, Imax becomes 255;

(5) N denotes a total number of pixels in one field, and if one frame consists of 640×480, then N=15360(=640×480/2); and (6) m is an index representing human's non-linear sensitivity as to the VDT seizure risk, and typically set to 1, 2, or 3.

If the weighting coefficients $w_R$, $w_G$, and $w_B$ are made different, it is possible to change the seizure risk index e(t) depending on the image colors. It is admitted that the red color flash is liable to induce the VDT stress symptoms, and as such, if the weighting coefficient $W_R$ is made large relative to $w_G$, and $w_B$, the red color flash can be reflected on the seizure risk index e(t). Further, the index e(t) is normalized in equation (2) by the total number of pixels in one field, and thus it is possible to reduce undesirable influence due to the differences of display screen sizes.

As mentioned above, the seizure risk index e(t) is determined based on the differences between the cumulated pixel values (stored in the field memory 30) and the pixel values of one field (stored in the filed memory 22), and accordingly, the second prior art suffers from the difficulty that the risk index e(t) erroneously indicates a high value due to white noise and/or contours of picture images irrespective of fact that the possibility of inducing the stress symptoms is extremely low. In other words, the second prior art is unable to correctly evaluate the VDT seizure risk based on the human's visual sensation.

More specifically, for example, in case white noise is superimposed on the original primary-color signals, the differences between the corresponding pixel data stored in the field memories 22 and 30 become large, resulting in erroneously indication of the seizure risk possibility.

By way of example, in the case where half of the pixels in the frames flashes, if the flashing pixels are randomly scattered over the frame, the seizure risk index e(t) indicates a high level irrespective of the fact that the VDT seizure risk is very low. On the contrary, in the same case, if the flashing pixels are concentrated on half of each of the frames, the index e(t) becomes high because the seizure risk is high. However, the second prior art is encountered the problem that the above-mentioned two cases are unable to be distinguished.

Further, it is often the case that the corresponding pixel values of the adjacent fields change abruptly at the contour of the picture images. In such an instance, the differences between the two field signals stored in the memories 22 and 30 become large, leading to an undesirable result of erroneously increasing the VDT seizure risk. The aforesaid prior art also suffers from the difficulty of being unable to deal with such a case.

SUMMARY OF THE INVENTION

It is therefore an object of the present invention to provide techniques for properly indexing VDT seizure risks induced by violent flashing lights on the video display screen.

In brief, the object is achieved by the technology wherein in order to generate a risk index of stress symptoms triggered by flashing lights on a scan type video display screen, a video signal processor is provided which operates such as to implement temporal filtering and spatial filtering on a video signal applied thereto every field and detect low temporal frequency components while excluding effects due to high spatial frequencies. A risk index generator receives the low frequency components from the video signal processor and determines the risk index based thereon.

One aspect of the present invention resides in a system for generating a risk index of seizures induced by flashing lights on a scan type video display screen, comprising: video signal processing means for implementing temporal filtering and spatial filtering on a video signal applied thereto every field or every frame and determining temporal low frequency components which are not associated with high spatial frequencies; and a risk index generator for determining the risk index using the temporal low frequency components issued from the video signal processing means and generating the risk index.

Another aspect of the present invention resides in a system for generating a risk index of seizures induced by flashing lights on a scan type video display screen, comprising; first video signal processing means for implementing temporal filtering and spatial filtering on an incoming video signal applied thereto every field or every frame and determining temporal low frequency components which are not associated with high spatial frequencies, and generating a first video signal; second video signal processing means for implementing temporal filtering on the incoming video signal applied thereto every field or every frame and determining temporal low frequency components, and generating a second video signal; and a risk index generator which receives the first and second video signals and determines the risk index using the first and second video signals and generating the risk index.

A still another aspect of the present invention resides in a system for generating a risk index of seizures induced by flashing lights on a scan type video display screen, comprising: a temporal low-pass filter for determining low temporal frequency components of an incoming video signal applied thereto every field or every frame; a memory for storing the incoming video signal applied thereto every field or every frame; a spatial frequency determiner for determining spatial frequencies of the video signal retrieved from the memory every field or every frame; and a risk index generator which receives data from the temporal low-pass filter, the memory, and the spatial frequency determiner, and determines and generates the risk index using the received data.

A still another aspect of the present invention resides in a method of generating a risk index of seizures induced by flashing lights on a scan type video display screen, comprising the steps of: (a) implementing temporal filtering and spatial filtering on a video signal every field or every frame and determining temporal low frequency components which are not associated with high spatial frequencies; and (b) determining the risk index using the temporal low frequency components obtained at step (a) and generating the risk index.

A still another aspect of the present invention resides in a method of generating a risk index of seizures induced by flashing lights on a scan type video display screen, comprising the steps of: (a) implementing temporal filtering and spatial filtering on an incoming video signal every field or every frame and determining temporal low frequency components which are not associated with high spatial frequencies; (b) implementing temporal filtering on the incoming video signal every field or every frame and determining temporal low frequency components; and (c) determining the risk index using the video signal processed at steps (a) and (b).

A still another aspect of the present invention resides in a method of generating a risk index of seizures induced by flashing lights on a scan type video display screen, comprising: (a) determining low temporal frequency components of an incoming video signal applied thereto every field or every frame; (b) temporarily storing the incoming video signal applied thereto every field or every frame; (c) determining spatial frequencies of the video signal retrieved from the memory every field or every frame; and (d) determining the risk index using the data determined or stored at steps (a), (b), and (c).

A still another aspect of the present invention resides a method of generating a risk index of seizures induced by flashing lights on a scan type video display screen, comprising: (a) determining low temporal frequency components of an incoming video signal applied thereto every field or every frame; (b) temporarily storing the incoming video signal applied thereto every field or every frame; (c) deter g spatial frequencies of the video signal retrieved from the memory every field or every frame, and determining a medium value or a maximal value of the detected spatial frequencies; and (d) determining the risk index using the data determined or stored at steps (a), (b), and (c).

BRIEF DESCRIPTION OF THE DRAWINGS

The features and advantages of the present invention will become more clearly appreciated from the following description taken in conjunction with the accompanying drawings in which like elements or portions are denoted by like reference numerals and in which:

FIG. 3 is a diagram schematically showing spatial frequency low-pass filter of FIG. 2;

DETAILED DESCRIPTION OF THE PREFERRED EMBODIMENTS

Figure 1:
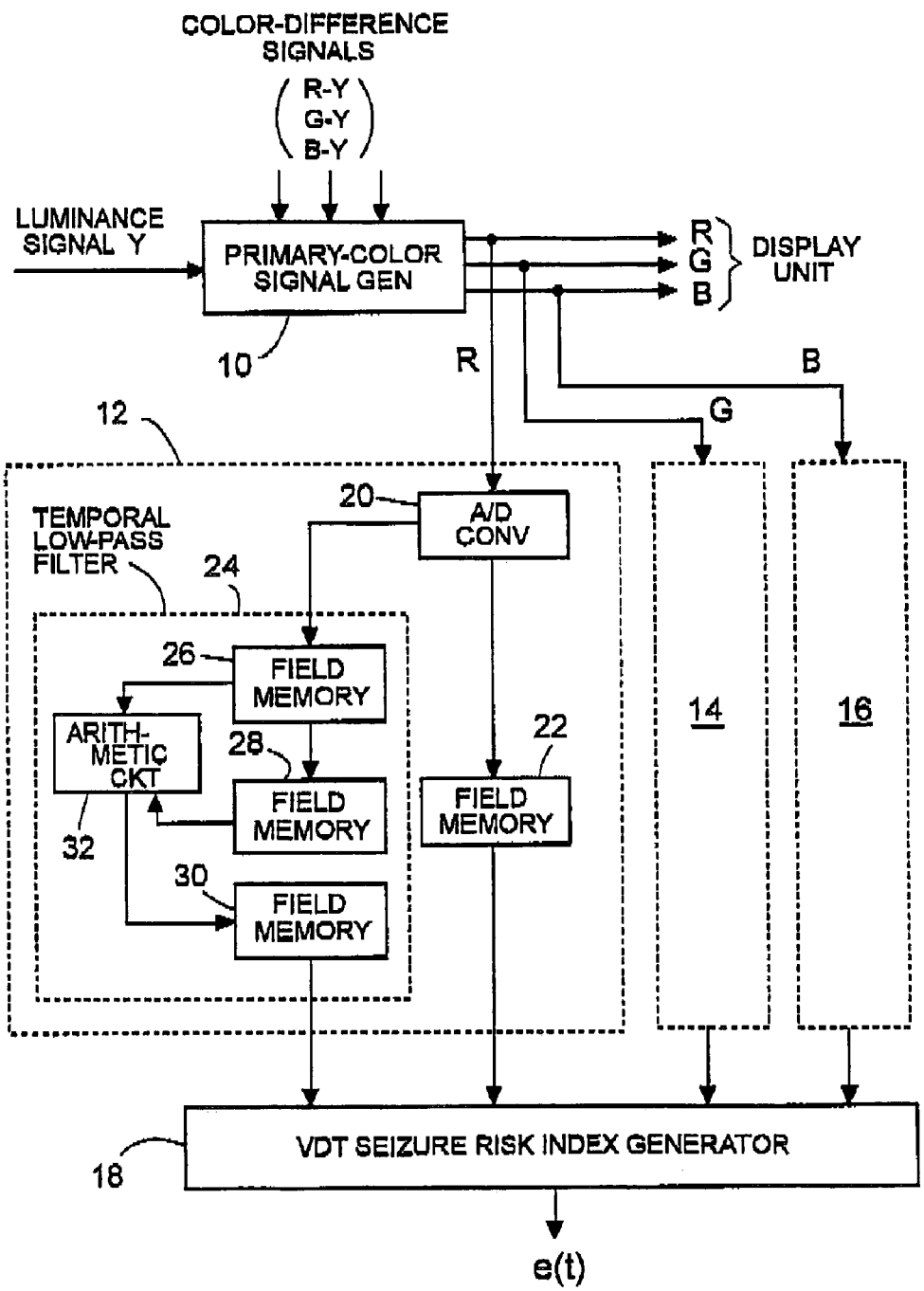
FIG. 1 is a diagram schematically showing a VDT seizure risk indexing system together with related portions of a television receiver set, having been described in the opening paragraphs.

Preferred embodiments of the present invention will be described. The present invention can be realized by way of hardware or software, The following descriptions will focus on the indexing of a VDT seizure risk regarding the interlaced scanning, but applicable to the case of the non-interlaced scanning as well. The present invention is based on the second prior art so as to solve the problems inherent therein, which problems arises from the fact that the VDT seizure risk is determined only using a temporal low-pass filter. The conventional techniques already referred to above will be omitted for the sake of simplifying the instant disclosure.

A first embodiment of the present invention will be described with reference to FIGS. 2 and 3. In the following, the portions identical to those described regarding FIG. 1 are denoted by the same reference numerals.

Figure 2:
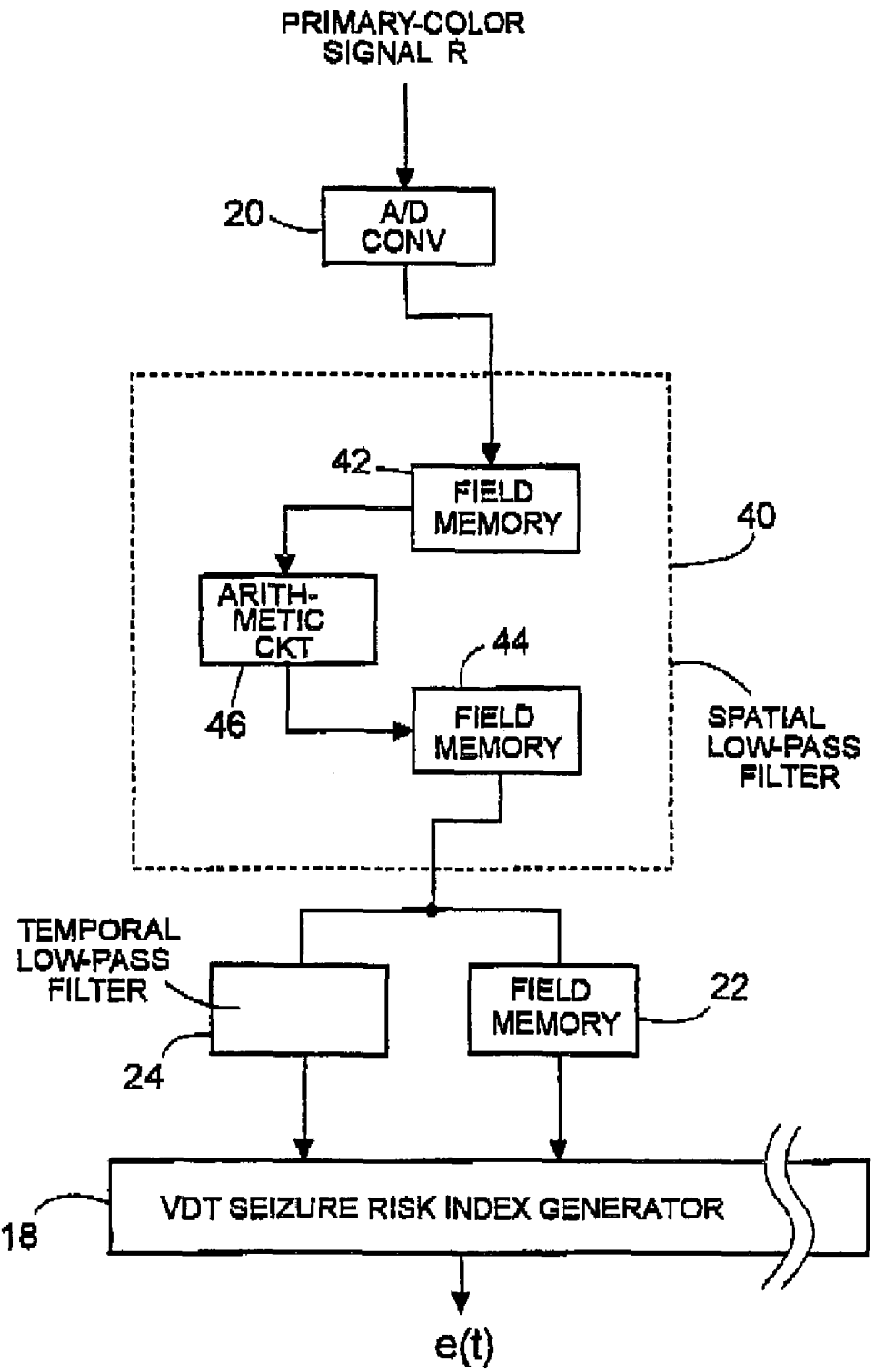
FIG. 2 is a diagram schematically showing a VDT seizure risk indexing system according to a first embodiment of the present invention.

In FIG. 2, the signal processing sections, to which the three primary-color signals R, G, and B are respectively applied, are substantially identical with one another, and thus, only the signal processing section associated with the primary-color signal R is illustrated in detail.

As shown in FIG. 2, the first embodiment differs from the prior art of FIG. 1 in that a spatial low-pass filter 40 is inserted immediately after the A/D converter 20, and the output of the spatial low-pass filter 40 is applied to the temporal low-pass filter 24 and the field memory 22. The spatial low-pass filter 40 comprises two field memories 42 and 44 and an arithmetic circuit 46 in this particular case, and removes high spatial frequency components of the incoming digital signal. In other words, the filter 40 is to smooth the field image. As is known in the art, the spatial frequencies are periods of pixel values in the field.

As in the prior art discussed with reference to FIG. 1, the primary-color signal (analog) R is converted into the corresponding digital signal at the analog-to-digital converter 20 without distinguishing the adjacent fields (viz., odd and even fields). The field signal of prima-color R thus digitized is successively stored one by one in the field memory 42.

FIG. 3 shows one example of the operation of the spatial low-pass filter 40. The arithmetic circuit 46 retrieves pixel values in a predetermined square area or a rectangular area (6×6 pixel values in the case shown in FIG. 3) from the field memory 42, and perform convolutional computation on the retrieved pixel values using a low-pass filter coefficient (3×3 pixels in the case shown in FIG. 3) previously stored in the arithmetic unit 46. This operation is implemented on the entire pixel values of the field signal stored in the memory 42, and successively applies the outputs thereof to the field memory 44. The filter coefficient shown in FIG. 3 is exemplary and is practically determined considering the field signal applied to the arithmetic unit 46. In the above, it is without saying that the pixel values loaded into the arithmetic unit 46 is not limited to 6×6 pixel values. The filtering (or smoothing) operations of the pixel values in the vicinity of field edges can be implemented using a conventional technology.

Since the spatial low-pass filter 40 operates such as to smooth the pixel values two-dimensionally, it is possible to remove the high spatial frequency components in the direction normal to the scanning lines and also in parallel therewith. It is understood that the highest spatial frequency in the direction perpendicular to the scanning lines corresponds to the interval between the adjacent scanning lines.

The spatial low-pass filter 40 is able to remove high frequency components resulting from white noise or the contours of the picture images, Such high frequency components are unlikely to induce the VDT seizures. Accordingly, in the case where the field signal from which the high frequency components have been removed is applied to the temporal low-pass filter 24 and the field memory 22, it is possible to obtain a highly reliable VDT seizure risk index e(t).

Figure 4:
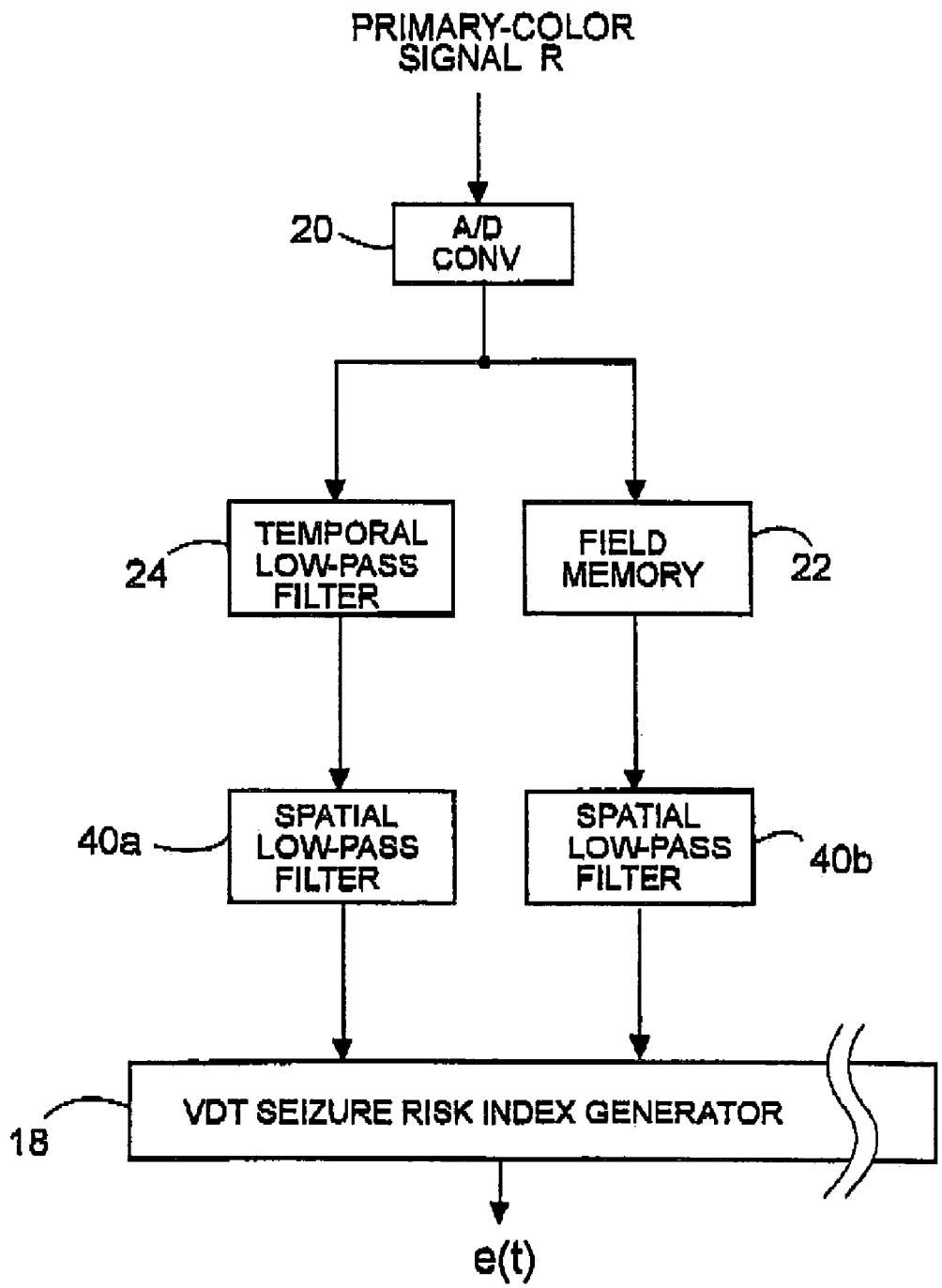
FIG. 4 is a diagram schematically showing a variant of the first embodiment shown in FIG. 2.

Referring to FIG. 4, a modification of the first embodiment is schematically illustrated. As shown in FIG. 4, the output of the analog-to-digital converter 20 is split into two signals, one of which is subject to the temporal low-pass filtering at the filter 24 and then is subject to the spatial low-pass filtering at a filter 40a, and the other of which is temporarily stored in the field memory 22 and then applied to a spatial low-pass filter 40b. Each of the spatial low-pass filters 40a and 40b is configured in a manner similar to the filter 40 already described with reference to FIG. 2. The modification of FIG. 4 is to implement the spatial low-frequency filtering (or smoothing) on the two split digital field signals, and other than this, is substantially identical to the first embodiment shown in FIG. 2. As an alternative of the above modification, it is possible to provide the two spatial low-pass filters 40a and 40b such as to precede the temporal low-pass filter 24 and the field memory 22, respectively. The operation of the modification of FIG. 4 is readily understandable from the foregoing, and thus further descriptions thereof will be omitted for brevity.

Figure 5A:
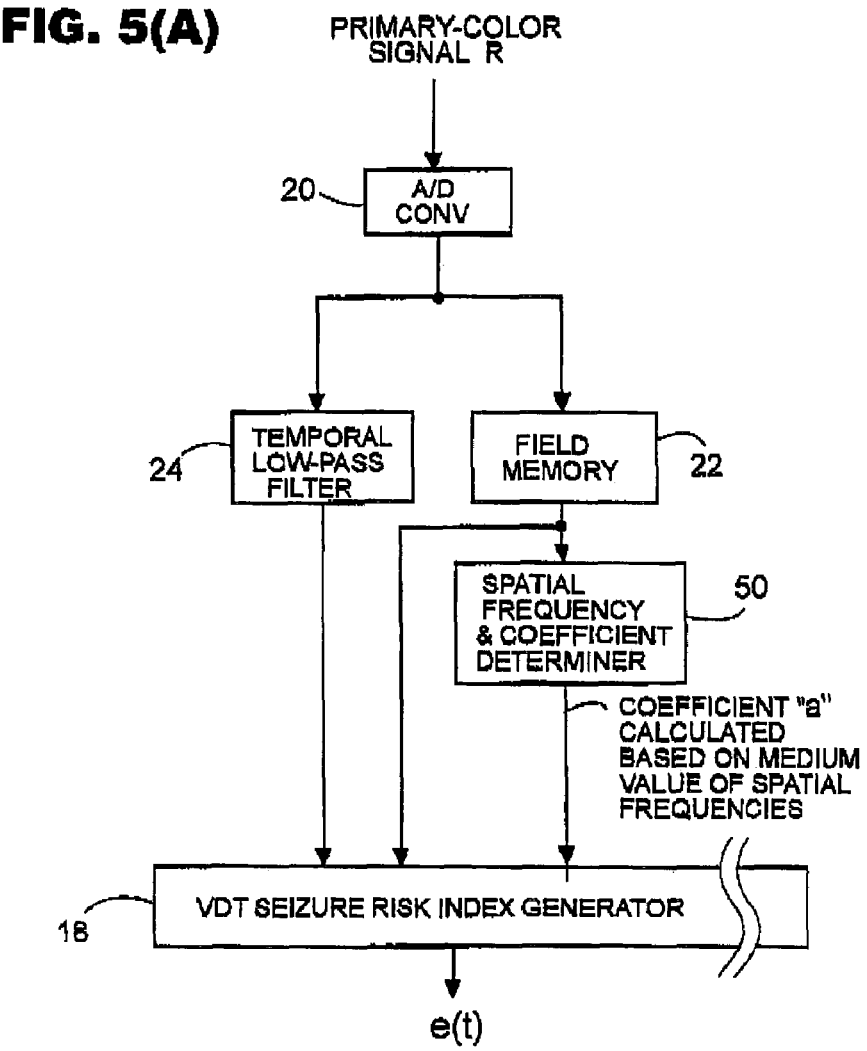
FIG. 5(A) is a diagram schematically showing a second embodiment of the present invention.
Figure 5B:
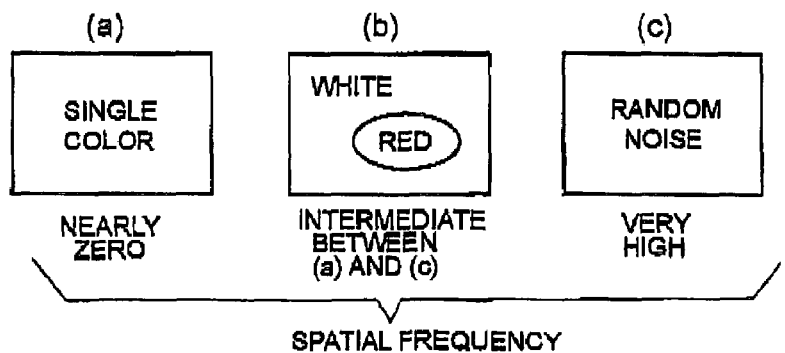
FIG. 5(B) is sketches for use in describing the operation of the second embodiment of FIG. 5(A).

FIG. 5(A) is a diagram schematically showing a second embodiment of the present invention, and FIG. 5(B) is sketches for describing the operation of the second embodiment.

As shown in FIG. 5(A), the second embodiment is provided with a spatial frequency and coefficient determiner 50 which immediately follows the field memory 22. The output of the spatial frequency and coefficient determiner 50 is applied to the DVT seizure risk index generator 18. Other than this, the second embodiment is substantially identical to the prior art of FIG. 1. More specifically, the spatial frequency and coefficient determiner 50 determines spatial frequencies of pixel values of each field signal, and then determines a coefficient $\alpha$ ($0<\alpha\leq 1$) based on the medium value or the maximal value of the determined special frequencies. The DVT seizure risk index generator 18 is supplied with the coefficient $\alpha$, and also supplied with the pixel data from the temporal low-pass filter 24 and the field memory 22 as in the case of FIG. 1, and then multiplies the risk index calculated using equation (2) by the coefficient $\alpha$. The calculation result is outputted from the generator 18.

As shown in part (a) of FIG. 5(B), if the spatial frequency determiner 50 is supplied with a field image signal indicating that the whole field image is of a single color (red, white, etc.), the spatial frequencies of this field, which are detected at the determiner 50, are approximately zero. In this instance, during the subsequent fields, the entire screen image flashes in the range of 2–55 Hertz (for example), the possibility of inducing the DVT seizures becomes considerably high. In such a case, the coefficient $\alpha$ takes a value of 1 or nearly 1.

On the other hand, as shown in part (c) of FIG. 5(B), if the spatial frequency and coefficient determiner 50 is supplied with a field image signal including random noise which cover the entire display screen, the spatial frequencies of this field, which are detected at the determiner 50, is very high. In this instance, the possibility of inducing the DVT seizures is very low, and thus, the coefficient $\alpha$ takes a low value in the vicinity of zero.

Further, as shown in part (b) of FIG. 5(B), if the spatial frequency determiner 50 is supplied with a field image signal indicating that a red colored area exists on the background of white, relatively high spatial frequencies are detected at the contour of the red colored area. However, the medium value of the spatial frequencies of the entire field is not so high compared with the case (c) of FIG. 5(B). In this case, if the red colored area flashes at the subsequent fields, there is a relatively high possibility of inducing the DVT seizures, which is however not so high compared to the case shown in part (a) of FIG. 5(B). In this instance, the coefficient $\alpha$ takes an intermediate value of those of the cases (a) and (c) of FIG. 5(B). The coefficient $\alpha$ is determined considering the size of the single colored area, the size of the display screen in use, etc.

In the above, it is possible to apply the medium value or the maximal value of the spatial frequencies, in place of the coefficient $\alpha$, to the generator 18, in the case of which the VDT seizure risk index generator 18 determines the risk index e(t) considering the spatial frequency data applied thereto.

In the aforesaid embodiments of the present invention, the DVT seizure risk index generator 18 issues the seizure risk index e(t) every field signal. However, although not shown in the drawings, it is preferable to provide a DVT seizure risk evaluator which is preceded by the VDT seizure risk index generator 18. More specifically, unless the issuance of the risk index signals each exceeding a predetermined threshold level continues for a relative long time period (for example more than one or two seconds), it is conceivable in some cases the possibility of inducing the VDT seizures might be not so high. It is therefore preferable to add the above-mentioned DVT seizure risk evaluator to the first and second embodiments and also to the variant of the first embodiment.

In the above, the primary-color signals R, G, and B are utilized to generate the VDT seizure risk index e(t). However, it is possible to use the luminance signal Y which, in this case, is applied to the signal processing sections in place of the primary-color signals R, G, and B.

Further, in the foregoing, the DVT seizure risk index is detected using field signals. However, it is in the scope of the present invention to use the DVT seizure risk index every frame.

The foregoing descriptions show one preferred embodiment and some modifications thereof. However, other various modifications are apparent to those skilled in the art without departing from the scope of the present invention which is only limited by the appended claims. Therefore, the embodiments and modification shown and described are only illustrated, not restrictive.

What is claimed is:

1. A system for generating a risk index of seizures induced by flashing lights on a scan type video display screen, comprising:

video signal processing means for implementing temporal filtering and spatial filtering on a video signal applied thereto every field or every frame and determining temporal low frequency components which are not associated with high spatial frequencies; and a risk index generator for determining the risk index using only the temporal low frequency components which are not associated with high spatial frequencies issued from the video signal processing means and generating the risk index.

2. The system as claimed in claim 1, wherein the video signal to be processed at the video signal processing means is primary-color signals or a luminance signal.

3. The system as claimed, in claim 1, further comprising a risk index evaluator being provided such as to receive the risk index issued from the risk index generator, the risk index evaluator filtering the risk index which continues a predetermined time period while exceeding a predetermined threshold.

4. A system for generating a risk index of seizures induced by flashing lights on a scan type video display screen, comprising:

first video signal processing means for implementing temporal filtering and spatial filtering on an incoming video signal applied thereto every field or every frame and determining temporal low frequency components which are not associated with high spatial frequencies, and generating a first video signal using only the temporal low frequency components which are not associated with high spatial frequencies;

second video signal processing means for implementing temporal filtering on the incoming video signal applied thereto every field or every frame and determining temporal low frequency components, and generating a second video signal; and a risk index generator which receives the first and second video signals and determines the risk index using the first and second video signals and generating the risk index.

5. The system as claimed in claim 4, wherein the video signal to be processed at each of the first and second video signal processing means are primary-color signals or a luminance signal.

6. The system as claimed in claim 4, further comprising a risk index evaluator being provided such as to receive the risk index issued from the risk index generator, the risk index evaluator filtering the risk index which continues a predetermined time period while exceeding a predetermined threshold.

7. A system for generating a risk index of seizures induced by flashing lights on a scan type video display screen, comprising:
a temporal low-pass filter for determining low temporal frequency components of an incoming video signal applied thereto every field or every frame;
a memory for storing the incoming, video signal applied thereto every field or every frame;
a spatial frequency determiner for determining spatial frequencies of the video signal retrieved from the memory every field or every frame; and
a risk index generator which receives data from the temporal low-pass filter, the memory, and the spatial frequency determiner, and determines and generates the risk index using the received data.

8. The system as claimed in claim 7, wherein the spatial frequency determiner issues a coefficient indicating a medium value or a maximal value of the determined spatial frequencies, and applies the medium value or the maximal value to the risk index generator, and wherein the risk index generator determines the risk index using the medium value or the maximal value of the determined spatial frequencies.

9. The system as claimed in claim 7, wherein the incoming signal is primary-color signals or a luminance signal.

10. The system as claimed in claim 7, further comprising a risk index evaluator being provided such as to receive the risk index issued from the risk index generator, the risk index evaluator filtering the risk index which continues a predetermined time period while exceeding a predetermined threshold.

11. A method of generating a risk index of seizures induced by flashing lights on a scan type video display screen, comprising the steps of:
(a) implementing temporal filtering and spatial filtering on a video signal every field or every frame and determining temporal low frequency components which are not associated with high spatial frequencies; and
(b) determining the risk index using only the temporal low frequency components obtained at step (a) and generating the risk index.

12. The method as claimed in claim 11, wherein the video signal is primary-color signals or a luminance signal.

13. The method as claimed in claim 11, further comprising:
evaluating the risk index determined at step (b) by filtering the risk index which continues a predetermined time period while exceeding a predetermined threshold.

14. A method of generating a risk index of seizures induced by flashing lights on a scan type video display screen, comprising the steps of:
(a) implementing temporal filtering and spatial filtering on an incoming video signal every field or every frame and determining temporal low frequency components which are not associated with high spatial frequencies;
(b) implementing temporal filtering on the incoming video signal every field or every frame and determining temporal low frequency components; and
(c) determining the risk index using the video signal processed at steps (a) and (b).

15. The method as claimed in claim 14, wherein the video signal to be processed at steps (a) and (b) is primary-color signals or a luminance signal.

16. The method as claimed in claim 14, further comprising:
evaluating the risk index determined at step (c) by filtering the risk index which continues a predetermined time period while exceeding a predetermined threshold.

17. A method of generating a risk index of seizures induced by flashing lights on a scan type video display screen, comprising:
(a) determining low temporal frequency components of an incoming video signal applied thereto every field or every frame;
(b) temporarily storing the incoming video signal applied thereto every field or every frame;
(c) determining spatial frequencies of the video signal retrieved from the memory every field or every frame; and
(d) determining the risk index using the data determined or stored at steps (a), (b), and (c).

18. The method as claimed in claim 17, wherein the incoming signal is primary-color signals or a luminance signal.

19. The method as claimed in claim 17, further comprising:
evaluating the risk index determined at step (d) by filtering the risk index which continues a predetermined time period while exceeding a predetermined threshold.

20. A method of generating a risk index of seizures induced by flashing lights on a scan type video display screen, comprising:
(a) determining low temporal frequency components of an incoming video signal applied thereto every field or every frame;
(b) temporarily storing the incoming video signal applied thereto every field or every frame;
(c) determining spatial frequencies of the video signal retrieved from the memory very field or every frame, and determining a medium value or a maximal value of the detected spatial frequencies; and
(d) determining the risk index using the data determined or stored at steps (a), (b), and (c).

21. The system of claim 1, wherein said video signal processing means includes a spatial low-pass filter that filters out the high spatial frequencies.

22. The system of claim 4, wherein said first video signal processing means includes a spatial low-pass filter that filters out the high spatial frequencies.

23. The method of claim 11, wherein the spatial filtering includes low-pass filtering that filters out the high spatial frequencies on the video signal every field or every frame to determine the temporal low frequency components which are not associated with high spatial frequencies.

24. The method of claim 14, wherein the step of spatial filtering includes low-pass filtering that filters out the high spatial frequencies on the video signal every field or every frame to determine the temporal low frequency components which are not associated with high spatial frequencies.

25. The method of claim 17, wherein the step of determining spatial frequencies includes low-pass filtering that filters out the high spatial frequencies of the video signal retrieved from the memory every field or every frame.

* * * * *